United States Patent
Chen

(10) Patent No.: US 11,794,853 B2
(45) Date of Patent: Oct. 24, 2023

(54) ELECTRIC BICYCLE ASSISTANCE CONTROLLING METHOD AND ASSISTANCE CONTROLLING SYSTEM

(71) Applicant: DARAD INNOVATION CORPORATION, Taoyuan (TW)

(72) Inventor: Wen-Yen Chen, Taoyuan (TW)

(73) Assignee: DARAD INNOVATION CORPORATION, Taoyuan (TW)

( * ) Notice: Subject to any disclaimer, the term of this patent is extended or adjusted under 35 U.S.C. 154(b) by 556 days.

(21) Appl. No.: 17/137,254

(22) Filed: Dec. 29, 2020

(65) Prior Publication Data

US 2021/0309319 A1 Oct. 7, 2021

(30) Foreign Application Priority Data

Apr. 1, 2020 (TW) .................................. 109111169

(51) Int. Cl.
| | | |
|---|---|---|
| *B62M 6/50* | (2010.01) | |
| *A61B 5/02* | (2006.01) | |
| *A61B 5/00* | (2006.01) | |
| *A61B 5/024* | (2006.01) | |

(52) U.S. Cl.
CPC ............... *B62M 6/50* (2013.01); *A61B 5/024* (2013.01); *A61B 5/6895* (2013.01)

(58) Field of Classification Search
CPC ...... A61B 5/024; A61B 5/6895; B62J 45/416; B62M 6/40; B62M 6/50
See application file for complete search history.

(56) References Cited

U.S. PATENT DOCUMENTS

| | | | |
|---|---|---|---|
| 7,357,209 B2 | 4/2008 | Kokatsu | |
| 7,386,482 B2 | 6/2008 | Kokatsu | |
| 8,602,149 B2 | 12/2013 | Krieger | |
| 9,611,002 B1 * | 4/2017 | Shum ....................... | B62M 6/90 |
| 2005/0140113 A1 * | 6/2005 | Kokatsu ............. | A63B 22/0605 |
| | | | 280/205 |
| 2005/0246152 A1 * | 11/2005 | Kokatsu ............. | G06Q 30/0623 |
| | | | 703/22 |
| 2009/0181826 A1 | 7/2009 | Turner | |

(Continued)

FOREIGN PATENT DOCUMENTS

| | | |
|---|---|---|
| CN | 103010390 A | 4/2013 |
| CN | 203186536 U | 9/2013 |

(Continued)

*Primary Examiner* — Tyler J Lee
(74) *Attorney, Agent, or Firm* — Winston Hsu

(57) ABSTRACT

An electric bicycle assistance controlling method and an assistance controlling system are applied to an operation processor of an electric bicycle. The electric bicycle assistance controlling method includes defining several health levels and a first power interval and a second power interval, acquiring one health level and a target heart rate interval, and measuring a current human power and a current heart rate. When the current heart rate is within the target heart rate interval, the operation processor determines the assistance controlling system to output a second motor assistance in response to the current human power inside the first power interval, and determines the assistance controlling system to output a third motor assistance in response to the current human power inside the second power interval.

21 Claims, 5 Drawing Sheets

(56) References Cited

U.S. PATENT DOCUMENTS

2018/0154980 A1\* 6/2018 Lee .................. B60L 50/20
2019/0308690 A1\* 10/2019 Terashima ............. B62M 25/08

FOREIGN PATENT DOCUMENTS

| CN | 104147761 A | 11/2014 |
| CN | 107323592 A | 11/2017 |
| CN | 207773359 U | 8/2018 |
| CN | 108974230 A | 12/2018 |
| DE | 20 2005 008 190 U1 | 10/2005 |
| FR | 2 938 233 A1 | 5/2010 |
| JP | 2019-182227 A | 10/2019 |
| TW | I254014 | 5/2006 |
| TW | 201605680 A | 2/2016 |
| TW | 201733850 A | 10/2017 |
| TW | 201736187 A | 10/2017 |
| WO | 2014/169517 A1 | 10/2014 |
| WO | 2015/073791 A1 | 5/2015 |

\* cited by examiner

ELECTRIC BICYCLE ASSISTANCE CONTROLLING METHOD AND ASSISTANCE CONTROLLING SYSTEM

BACKGROUND OF THE INVENTION

1. Field of the Invention

The present invention relates to an electric bicycle assistance controlling method and an assistance controlling system, and more particularly, to an electric bicycle assistance controlling method capable of preventing sport injury and a related assistance controlling system.

2. Description of the Prior Art

A conventional electric bicycle has an assistance controlling system which utilizes a heart rate detector to detect a current heart rate of the user. If the current heart rate of the user is higher than a target heart rate interval, the assistance controlling system of the conventional electric bicycle increases the assistance to lessen human power and the heart rate of the user; however, the heart rate of the user may be lower than the target heart rate interval due to the increased assistance. If the current heart rate of the user is lower than the target heart rate interval, the assistance controlling system of the conventional electric bicycle decreases the assistance to raise the human power of the user so that the heart rate of the user approaches or enters the target heart rate interval; however, the heart rate of the user may exceed the target heart rate interval. Thus, the conventional assistance controlling system applied to the electric bicycle drives an assistance motor to output the assistance only according to the current heart rate of the user, and cannot effectively restrict the current heart rate within the target heart rate interval.

SUMMARY OF THE INVENTION

The present invention provides an electric bicycle assistance controlling method capable of preventing sport injury and a related assistance controlling system for solving above drawbacks.

According to the claimed invention, an electric bicycle assistance controlling method is applied to an operation processor of an electric bicycle, and the operation processor is electrically connected to a human power detector, a heart rate detector and an assistance motor of the electric bicycle. The electric bicycle assistance controlling method includes defining a plurality of preset health levels and a first power interval and a second power interval, acquiring one actual health level and determining the first power interval and the second power interval corresponding to the actual health level, acquiring a target heart rate interval, measuring a current human power by the human power detector and further measuring a current heart rate by the heart rate detector, and driving the assistance motor to output a second motor assistance in response to the current human power inside the first power interval or driving the assistance motor to output a third motor assistance in response to the current human power inside the second power interval when the current heart rate is within the target heart rate interval. The first power interval and the second power interval correspond to the plurality of preset health levels, and the second power interval is greater than the first power interval. The third motor assistance is greater than the second motor assistance.

According to the claimed invention, an assistance controlling system applied to an electric bicycle includes a human power detector, a heart rate detector, an assistance motor and an operation processor. The human power detector is adapted to measure a current human power. The heart rate detector is adapted to measure a current heart rate. The assistance motor is adapted to output a motor assistance with different levels. The operation processor is electrically connected to the human power detector, the heart rate detector and the assistance motor. The operation processor is adapted to define a plurality of preset health levels and a first power interval and a second power interval corresponding to the plurality of preset health levels, acquire one actual health level to determine the first power interval and the second power interval corresponding to the actual health level, acquire a target heart rate interval, and drive the assistance motor to output a second motor assistance in response to the current human power inside the first power interval or drive the assistance motor to output a third motor assistance in response to the current human power inside the second power interval when the current heart rate is within the target heart rate interval. The second power interval is greater than the first power interval, and the third motor assistance is greater than the second motor assistance.

The electric bicycle assistance controlling method and the assistance controlling system of the present invention can read and analyze the current heart rate and the current human power of the user to provide the applicable motor assistance. The current human power can represent a future trend of the heart rate variation of the user, which means the future heart rate may be rapidly increased when the current human power is high, and further means the future heart rate may be kept in constant or slowly decreased when the current human power is low. Therefore, the present invention can comprehensively analyze the current heart rate and the current human power of the user, so as to provide the applicable motor assistance for slowing changing the current heart rate into the target heart rate interval when the current heart rate is lower than the target heart rate interval, or to provide the applicable motor assistance in accordance with variation of the current human power for stably staying the current heart rate inside the target heart rate interval when the current heart rate is already within the target heart rate interval.

These and other objectives of the present invention will no doubt become obvious to those of ordinary skill in the art after reading the following detailed description of the preferred embodiment that is illustrated in the various figures and drawings.

DETAILED DESCRIPTION

Figure 1:
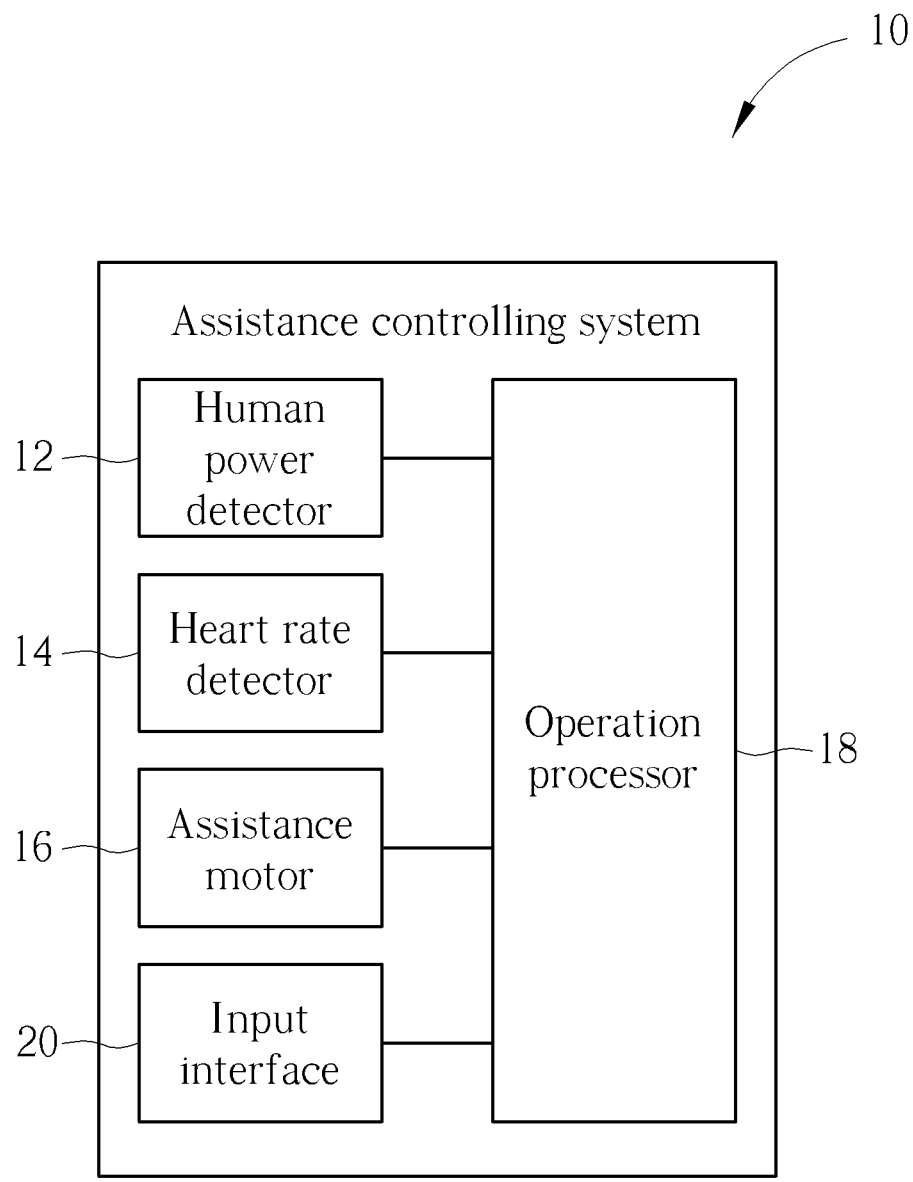
FIG. 1 is a functional block diagram of an assistance controlling system according to an embodiment of the present invention.
Figure 2:
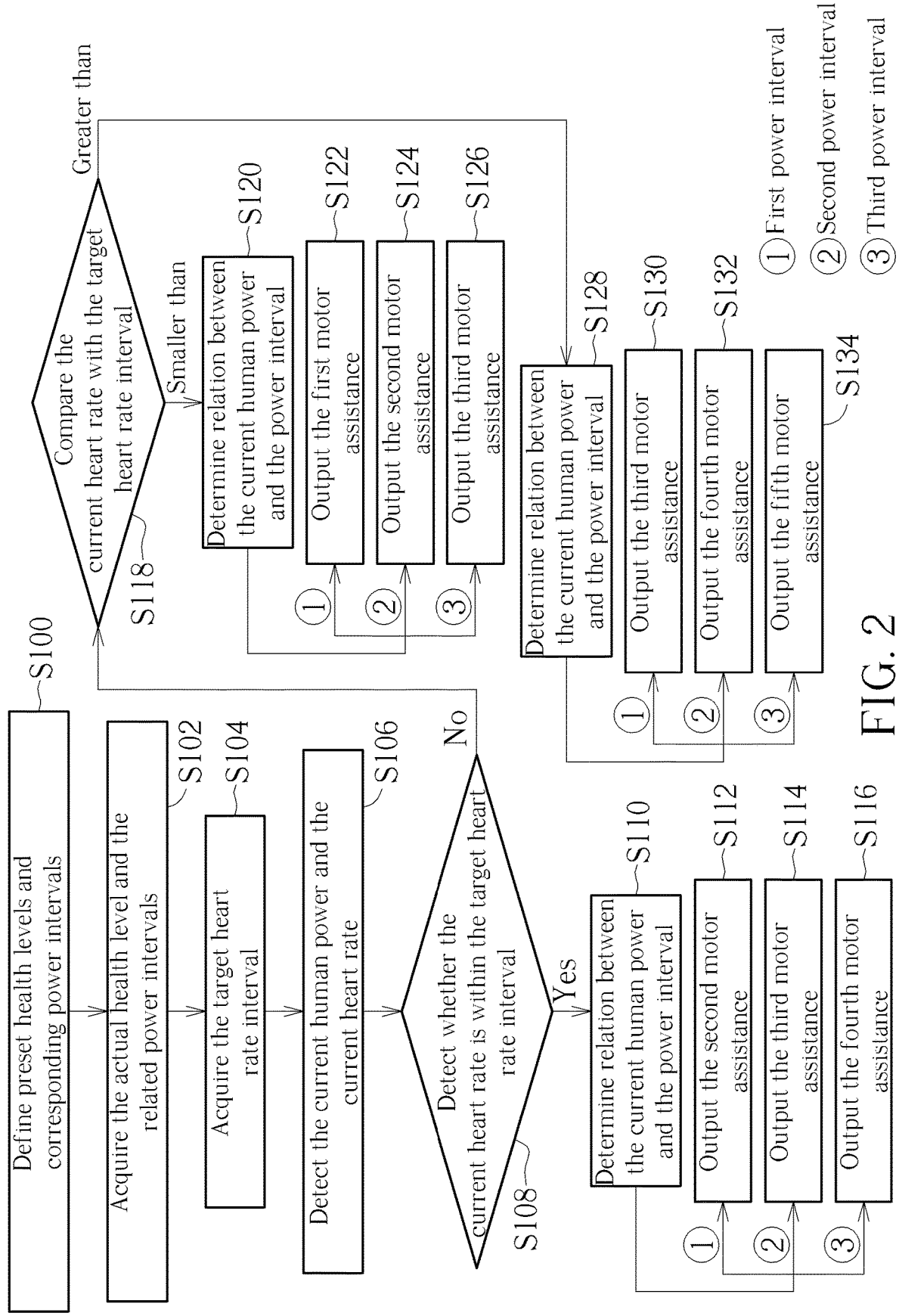
FIG. 2 is a flow chart of an electric bicycle assistance controlling method according to the embodiment of the present invention.

Please refer to FIG. 1 and FIG. 2. FIG. 1 is a functional block diagram of an assistance controlling system 10 according to an embodiment of the present invention. FIG. 2 is a flow chart of an electric bicycle assistance controlling method according to the embodiment of the present invention. The assistance controlling system 10 can be applied to an electric bicycle. The assistance controlling system 10 can include a human power detector 12, a heart rate detector 14, an assistance motor 16 and an operation processor 18. The human power detector 12 can be disposed on a foot pedal of the electric bicycle and used to detect a current human power of a user who rides the electric bicycle. The heart rate detector 14 can be disposed on a body of the user and used to detect a current heart rate. The assistance motor 16 can be connected to a wheel of the electric bicycle, and output motor assistance with a specific level according to an assistance computation result of the operation processor 18 for driving rotation of the wheel. The operation processor 18 can be electrically connected to the human power detector 12, the heart rate detector 14 and the assistance motor 16. The operation processor 18 can execute the electric bicycle assistance controlling method of the present invention and drive the assistance motor 16 to output the applicable motor assistance, for preventing the user from sport injury.

The assistance controlling system 10 can further include an input interface 20 electrically connected to the operation processor 18. The user can input an actual health level, an expected training intensity and a specific user datum via the input interface 20. The operation processor 18 can accurately determine the motor assistance according to health of the user. For example, the health level can be preset as including poor health, average health, good health and excellent health; the training intensity can be preset as including poor intensity, fair intensity, average intensity, good average and excellent intensity. The user datum can be an age, a weight and a resting heart rate of the user. Classification of the health level, the training intensity and the user datum of the present invention are not limited to the above-mentioned embodiments, which depend on an actual demand.

Figure 3:
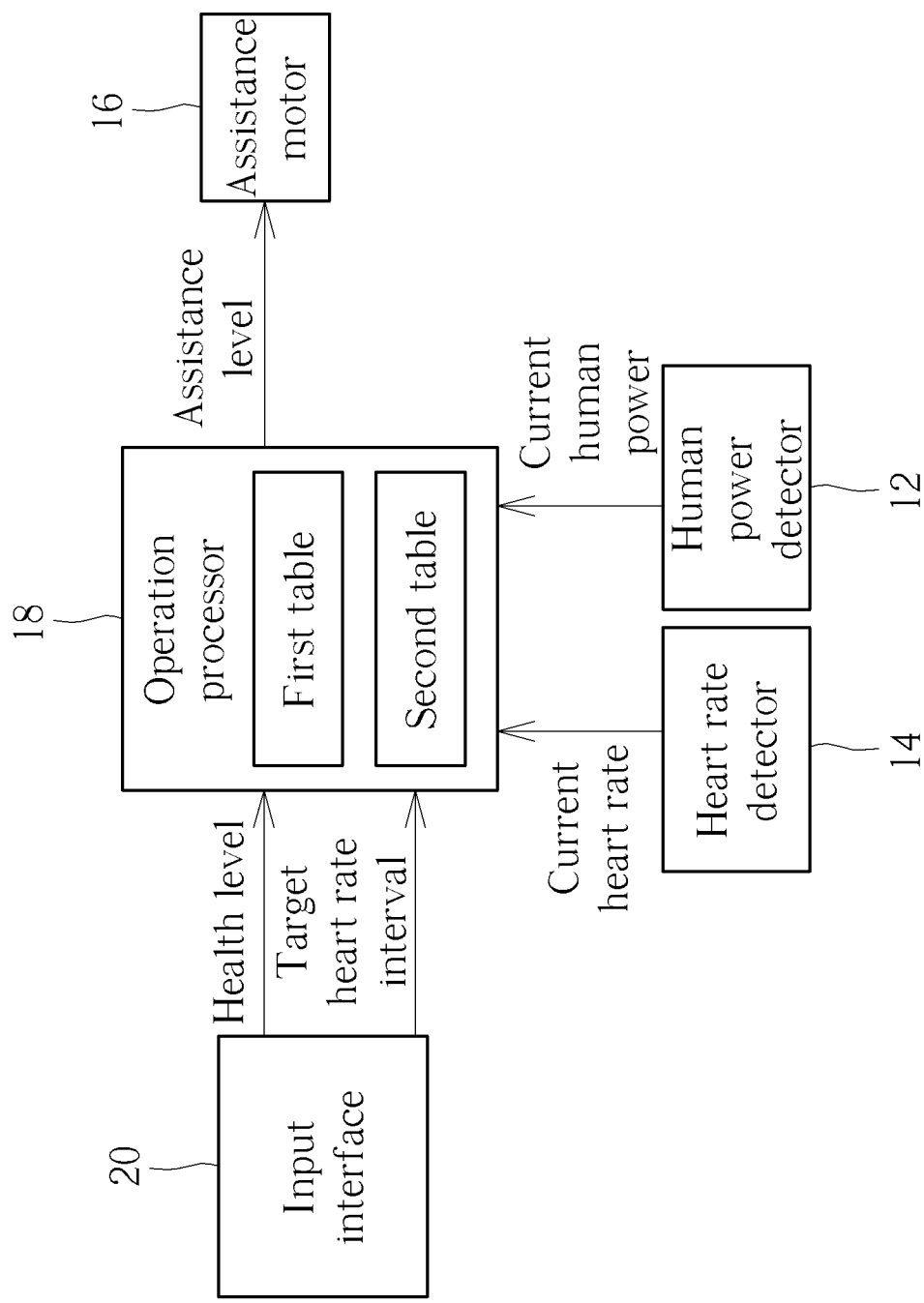
FIG. 3 is a functional block diagram of the electric bicycle according to the embodiment of the present invention.
Figure 4:
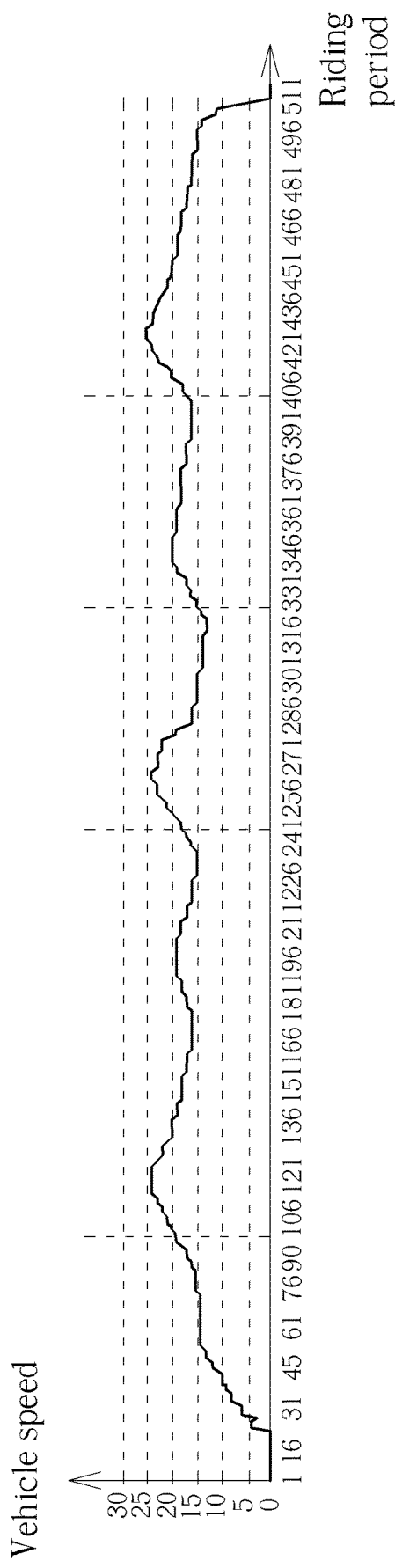
FIG. 4 is a diagram of relation between vehicle speed and a riding period of the electric bicycle according to the embodiment of the present invention.
Figure 5:
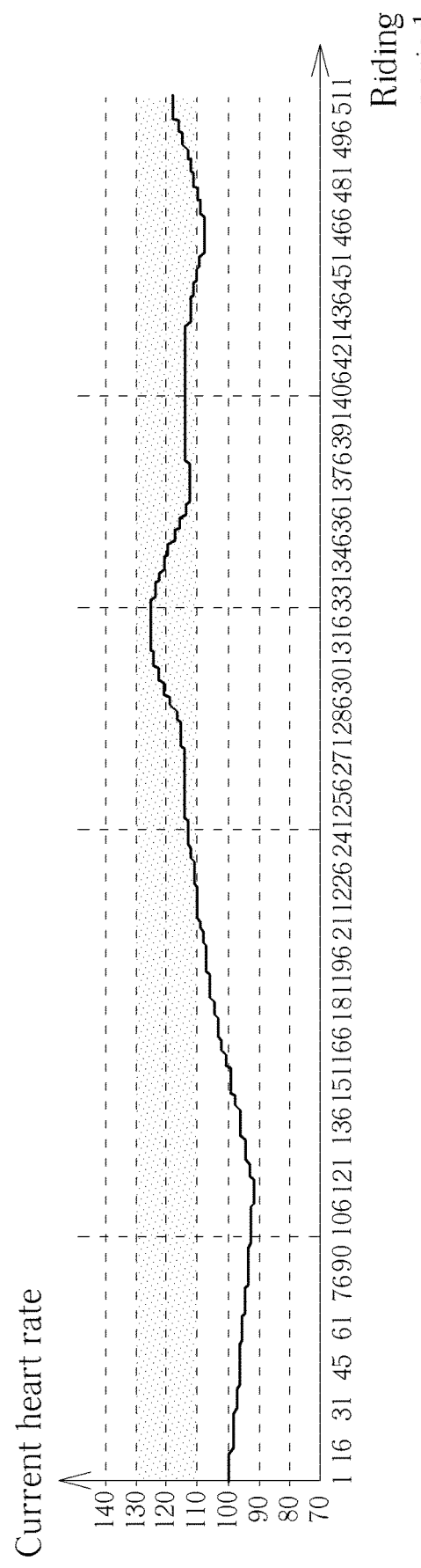
FIG. 5 is a diagram of relation between a current heart rate of the user and the riding period according to the embodiment of the present invention.
Figure 6:
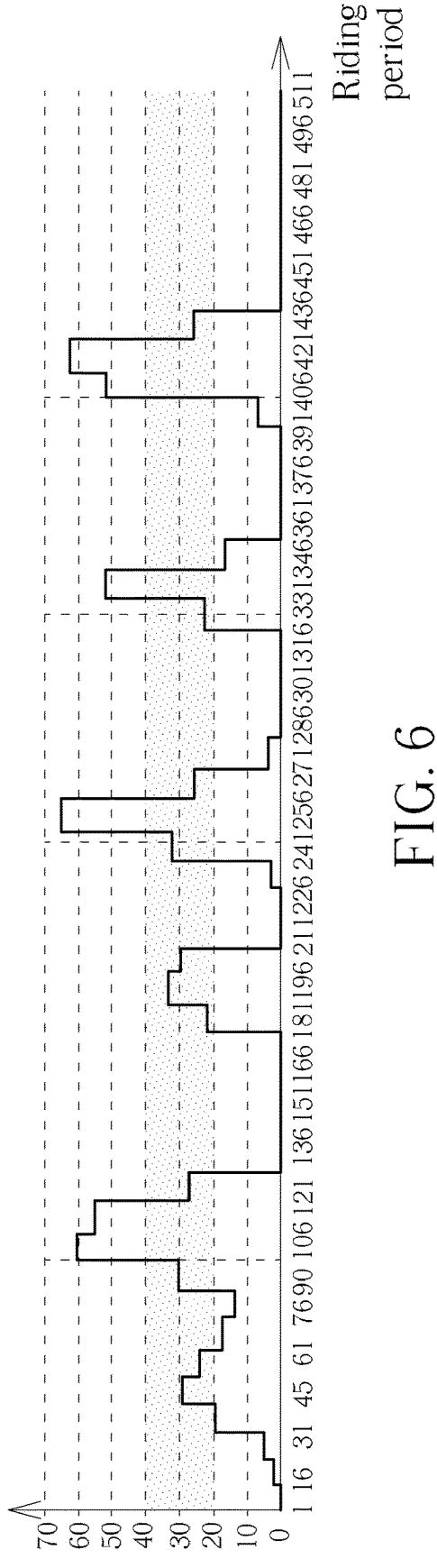
FIG. 6 is a diagram of relation between current human power of the user and the riding period according to the embodiment of the present invention.
Figure 7:
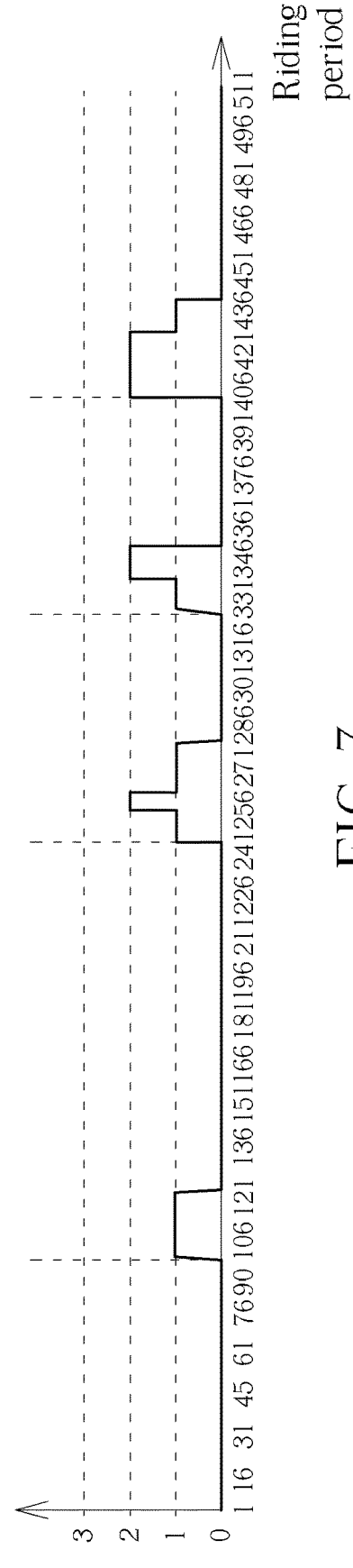
FIG. 7 is a diagram of relation between the motor assistance of the electric bicycle and the riding period according to the embodiment of the present invention.

Please refer to FIG. 2 to FIG. 4. FIG. 3 is a functional block diagram of the electric bicycle according to the embodiment of the present invention. FIG. 4 is a diagram of relation between vehicle speed and a riding period of the electric bicycle according to the embodiment of the present invention. FIG. 5 is a diagram of relation between a current heart rate of the user and the riding period according to the embodiment of the present invention. FIG. 6 is a diagram of relation between current human power of the user and the riding period according to the embodiment of the present invention. FIG. 7 is a diagram of relation between the motor assistance of the electric bicycle and the riding period according to the embodiment of the present invention.

Each health level can correspond to a plurality of power intervals. For example, the present invention can set a first power interval for low level, a second power interval for middle level, and a third power interval for high level. The embodiment can define the poor health has the low level first power interval smaller than 20 watts, the middle level second power interval ranged between 20-40 watts, and the high level third power interval greater than 40 watts; and can further define the average health has the low level first power interval smaller than 50 watts, the middle level second power interval ranged between 50-150 watts, and the high level third power interval greater than 150 watts; and can further define the good health has the low level first power interval smaller than 150 watts, the middle level second power interval ranged between 150-250 watts, and the high level third power interval greater than 250 watts; and can further define the excellent health has the low level first power interval smaller than 350 watts, the middle level second power interval ranged between 350-450 watts, and the high level third power interval greater than 450 watts. A number and a value of the power interval are not limited to the above-mentioned embodiment, which depend on a design demand.

The embodiment can further define a tolerance percentage of the training intensity; the training intensity has the poor intensity set as 50-60 percent, the fair intensity set as 60-70 percent, the average intensity set as 70-80 percent, the good average set as 80-90 percent, and the excellent intensity set as 90-100 percent. The percentage of each training intensity is not limited to the above-mentioned embodiment, which depend on the design demand. Therefore, the assistance controlling system 10 can combine the training intensity selected by the user with the user datum, and compute a target heart rate interval conforming to the healthy condition of the user. The present invention can immediately detect the current human power and the current heart rate of the user when riding the electric bicycle, and then drive the assistance motor 16 to output the applicable motor assistance for restricting the current heart rate of the user within the target heart rate interval.

In addition, the assistance controlling system 10 can define a difference between the user age and a parameter (such as 220) as a maximum heart rate (MEM), and define a difference between the maximum heart rate and the resting heart rate (RHR) as a heart rate reserve (HRR), and further acquire a product of the heart rate reserve (HRR) and a preset training intensity, so as to compute and interpret an amount of the resting heart rate and the said product as the target heart rate interval. Computation of the target heart rate interval is not limited to the above-mentioned embodiment, which may be varied according to any factor such as a race and a gender, and other possible variation is omitted herein for simplicity.

The present invention can compare the current heart rate immediately acquired by the heart rate detector 14 with the target heart rate interval. If the current heart rate is continuously rose but does not exceed the heart rate interval, the motor assistance can be accordingly increased to prevent the heart rate from going beyond limits when the current human power is enlarged. If current heart rate is close to superior limit of the target heart rate interval, the motor assistance can be increased due to enlargement of the current human power, so that the current heart rate can be slowly increased to enter the target heart rate interval. If the current heart rate falls, the motor assistance can be increased or decreased according to variation of the current human power, and thus the heart rate of the user can be stably kept within the target heart rate interval.

In the embodiment, the assistance controlling system 10 can compute the difference $e_{hr}$ between the current heart rate and the target heart rate interval, and interpret a comparison result of the difference $e_{hr}$ with a threshold range of the heart rate reserve as a heart rate deviated level, and then determine the current heart rate is lower than, higher than or located within the target heart rate interval according to the heart rate deviated level. The threshold range can be a positive five percent or a negative five percent of the heart rate reserve. Determination of the current heart rate and the target heart rate interval of the present invention are not limited to the above-mentioned embodiment, and depend on the design demand.

The present invention can establish a first table about the heart rate deviated level, the power interval and the motor assistance. The assistance motor 16 can output the motor assistance with five levels. The first motor assistance can represent ten percent of operation efficiency provided by the assistance motor 16; the second motor assistance can represent twenty-five percent of the operation efficiency provided by the assistance motor 16; the third motor assistance can represent fifty percent of the operation efficiency provided by the assistance motor 16; the fourth motor assistance can represent seventy-five percent of the operation efficiency provided by the assistance motor 16; the fifth motor assistance can represent ninety percent of the operation efficiency provided by the assistance motor 16. The operation efficiency of each level of the motor assistance is not limited to the above-mentioned embodiment, and depends on the design demand. Conditions 1-3 in the first table can represent the current heart rate is lower than the target heart rate interval; conditions 4-6 in the first table can represent the current heart rate is within than the target heart rate interval; conditions 7-9 in the first table can represent the current heart rate is greater than the target heart rate interval.

FIRST TABLE

| Condition | Heart Rate Deviated Level | Power Interval | Motor Assistance |
|---|---|---|---|
| 1 | $-5\%HRR > e_{hr}$ | First power interval | First motor assistance |
| 2 | | Second power interval | Second motor assistance |
| 3 | | Third power interval | Third motor assistance |
| 4 | $-5\%HRR < e_{hr} < +5\%HRR$ | First power interval | Second motor assistance |
| 5 | | Second power interval | Third motor assistance |
| 6 | | Third power interval | Fourth motor assistance |
| 7 | $e_{hr} > +5\%HRR$ | First power interval | Third motor assistance |
| 8 | | Second power interval | Fourth motor assistance |
| 9 | | Third power interval | Fifth motor assistance |

Further, the present invention can establish a second table about the health level and the related power interval. Values of each power interval can be varied in accordance with the health level.

SECOND TABLE

| Health Level | First power interval | Second power interval | Third power interval |
|---|---|---|---|
| Poor Health | <20 W | 20 W~40 W | >40 W |
| Average Health | <50 W | 50 W~150 W | >150 W |
| Good Health | <150 W | 150 W~250 W | >250 W |
| Excellent Health | <350 W | 350 W~450 W | >450 W |

According to the electric bicycle assistance controlling method, step S100 can be executed to define a plurality of preset health levels and a plurality of corresponding power intervals. Then, steps S102 and S104 can be executed to acquire the actual or expected health level input by the user via the input interface 20, and to determine a power range of the first power interval, the second power interval and the third power interval corresponding to the input health level, so as to acquire the target heart rate interval computed by the user age and the resting heart rate. Then, steps S106 and S108 can be executed to utilize the human power detector 12 and the heart rate detector 14 to immediately detect the current human power and the current heart rate of the user, and then detect whether the current heart rate is within the target heart rate interval.

If the current heart rate is within the target heart rate interval, the different $e_{hr}$, is greater than the negative five percent and smaller than the positive five percent of the heart rate reserve, and step S100 can be executed to determine relation between the current human power and the power interval. If the current human power is within the first power interval, step S112 can be executed to output the second motor assistance by the assistance motor 16; If the current human power is within the second power interval, step S114 can be executed to output the third motor assistance by the assistance motor 16; If the current human power is within the third power interval, step S116 can be executed to output the fourth motor assistance by the assistance motor 16.

When the current heart rate is not within the target heart rate interval, step S118 can be executed to compare the current heart rate with the target heart rate interval. Step S120 can be executed to determine relation between the current human power and the power interval in response to the current heart rate lower than the target heart rate interval. If the current human power is within the first power interval, step S122 can be executed to output the first motor assistance by the assistance motor 16; If the current human power is within the second power interval, step S124 can be executed to output the second motor assistance by the assistance motor 16; If the current human power is within the third power interval, step S126 can be executed to output the third motor assistance by the assistance motor 16.

Step S128 can be executed to determine relation between the current human power and the power interval in response to the current heart rate greater than the target heart rate interval. If the current human power is within the first power interval, step S130 can be executed to output the third motor assistance by the assistance motor 16; If the current human power is within the second power interval, step S132 can be executed to output the fourth motor assistance by the assistance motor 16; If the current human power is within the third power interval, step S134 can be executed to output the fifth motor assistance by the assistance motor 16.

As shown in FIG. 4, the vehicle speed of the electric bicycle may be changed at random, so the assistance controlling system 10 can be used to indirectly control the heart rate of the user who riding the electric bicycle. As the embodiments shown in FIG. 5 to FIG. 7, as if the health level of the user belongs to the poor health level, the first power interval is smaller than 20 watts, and the second power interval is ranged between 20-40 watts, and the third power interval is greater than 40 watts; in mean time, the target heart rate interval can be ranged between 110-130 heartbeats per minute. When the user rides and then the current heart rate is lower than the target heart rate interval and the current human power is within the first power interval or the second power interval, the assistance motor 16 can output the low level motor assistance; the embodiment can mark the low level motor assistance as level 0. When the current human power is within the third power interval and the current heart rate is still lower than the target heart rate interval, the assistance motor 16 can output the middle level motor assistance, and therefore the heart rate of the user can be slowly increased; the embodiment can mark the middle level motor assistance as level 1, and the assistance motor 16 may optionally output the low level motor assistance when the current human power is changed into the second power interval. When the current human power is within the third power interval and the current heart rate enters the target heart rate interval, the assistance motor 16 can output the high level motor assistance to prevent the heart rate of the user from exceeding the target heart rate interval; the embodiment can mark the high level motor assistance as level 2, and the assistance motor 16 can optionally output the middle level motor assistance or low level motor assistance when the current human power is changed into the second power interval.

In conclusion, the electric bicycle assistance controlling method and the assistance controlling system of the present invention can read and analyze the current heart rate and the current human power of the user to provide the applicable motor assistance. The current human power can represent a future trend of the heart rate variation of the user, which means the future heart rate may be rapidly increased when the current human power is high, and further means the future heart rate may be kept in constant or slowly decreased when the current human power is low. Therefore, the present invention can comprehensively analyze the current heart rate and the current human power of the user, so as to provide the applicable motor assistance for slowing changing the current heart rate into the target heart rate interval when the current heart rate is lower than the target heart rate interval, or to provide the applicable motor assistance in accordance with variation of the current human power for stably staying the current heart rate inside the target heart rate interval when the current heart rate is already within the target heart rate interval.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An electric bicycle assistance controlling method applied to an operation processor of an electric bicycle, the operation processor being electrically connected to a human power detector, a heart rate detector and an assistance motor of the electric bicycle, the electric bicycle assistance controlling method comprising:
   defining a plurality of preset health levels and a first power interval and a second power interval, wherein the first power interval and the second power interval correspond to the plurality of preset health levels, and the second power interval is greater than the first power interval;
   acquiring one actual health level and determining the first power interval and the second power interval corresponding to the actual health level;
   acquiring a target heart rate interval;
   measuring a current human power by the human power detector and further measuring a current heart rate by the heart rate detector; and
   driving the assistance motor to output a second motor assistance in response to the current human power inside the first power interval, or driving the assistance motor to output a third motor assistance in response to the current human power inside the second power interval when the current heart rate is within the target heart rate interval;
   wherein the third motor assistance is greater than the second motor assistance.

2. The electric bicycle assistance controlling method of claim 1, further comprising:
   driving the assistance motor to output a first motor assistance in response to the current human power inside the first power interval, or driving the assistance motor to output the second motor assistance in response to the current human power inside the second power interval when the current heart rate is lower than the target heart rate interval;
   wherein the first motor assistance is smaller than the second motor assistance.

3. The electric bicycle assistance controlling method of claim 2, further comprising:
   defining a third power interval corresponding to the plurality of preset health levels; and
   driving the assistance motor to output the third motor assistance in response to the current human power inside the third power interval;
   wherein the second power interval is smaller than the third power interval.

4. The electric bicycle assistance controlling method of claim 1, further comprising:
   driving the assistance motor to output the third motor assistance in response to the current human power inside the first power interval, or driving the assistance motor to output a fourth motor assistance in response to the current human power inside the second power interval when the current heart rate is higher than the target heart rate interval;
   wherein the fourth motor assistance is greater than the third motor assistance.

5. The electric bicycle assistance controlling method of claim 4, further comprising:
   defining a third power interval corresponding to the plurality of preset health levels; and
   driving the assistance motor to output a fifth motor assistance in response to the current human power inside the third power interval;
   wherein the second power interval is smaller than the third power interval, and the fifth motor assistance is greater than the fourth motor assistance.

6. The electric bicycle assistance controlling method of claim 1, wherein acquiring the target heart rate interval comprises:
   acquiring a training intensity and a user datum; and
   analyzing relation between the training intensity and the user datum to compute the target heart rate interval conforming to the user datum.

7. The electric bicycle assistance controlling method of claim 6, wherein the user datum comprises a user age and a resting heart rate, the user age is used to compute a maximum heart rate, the maximum heart rate and the resting heart rate are used to compute a heart rate reserve, and the target heart rate interval is a computation result of the heart rate reserve, the training intensity and the resting heart rate.

8. The electric bicycle assistance controlling method of claim 7, wherein the electric bicycle assistance controlling method computes a difference between the current heart rate and the target heart rate interval, and compares the difference with a threshold range of the heart rate reserve so as to determine the current heart rate is lower than, higher than or within the target heart rate interval.

9. The electric bicycle assistance controlling method of claim 1, wherein the motor assistance with different levels represents different operation efficiency of the assistance motor.

10. The electric bicycle assistance controlling method of claim 1, further comprising:
  defining a third power interval corresponding to the plurality of preset health levels; and
  driving the assistance motor to output a fourth motor assistance in response to the current human power inside the third power interval;
  wherein the second power interval is smaller than the third power interval, and the fourth motor assistance is greater than the third motor assistance.

11. An assistance controlling system applied to an electric bicycle, the assistance controlling system comprising:
  a human power detector adapted to measure a current human power;
  a heart rate detector adapted to measure a current heart rate;
  an assistance motor adapted to output a motor assistance with different levels; and
  an operation processor electrically connected to the human power detector, the heart rate detector and the assistance motor, the operation processor being adapted to define a plurality of preset health levels and a first power interval and a second power interval corresponding to the plurality of preset health levels, acquire one actual health level to determine the first power interval and the second power interval corresponding to the actual health level, acquire a target heart rate interval, and drive the assistance motor to output a second motor assistance in response to the current human power inside the first power interval or drive the assistance motor to output a third motor assistance in response to the current human power inside the second power interval when the current heart rate is within the target heart rate interval;
  wherein the second power interval is greater than the first power interval, and the third motor assistance is greater than the second motor assistance.

12. The assistance controlling system of claim 11, further comprising:
  an input interface electrically connected to the operation processor and adapted to input the actual health level.

13. The assistance controlling system of claim 12, wherein the operation processor further acquires a training intensity and a user datum via the input interface, and analyzes relation between the training intensity and the user datum to compute the target heart rate interval conforming to the user datum.

14. The assistance controlling system of claim 13, wherein the user datum comprises a user age and a resting heart rate, the user age is used to compute a maximum heart rate, the maximum heart rate and the resting heart rate are used to compute a heart rate reserve, and the target heart rate interval is a computation result of the heart rate reserve, the training intensity and the resting heart rate.

15. The assistance controlling system of claim 14, wherein the operation processor further computes a difference between the current heart rate and the target heart rate interval, and compares the difference with a threshold range of the heart rate reserve so as to determine the current heart rate is lower than, higher than or within the target heart rate interval.

16. The assistance controlling system of claim 11, wherein the operation processor further drives the assistance motor to output a first motor assistance in response to the current human power inside the first power interval, or drives the assistance motor to output the second motor assistance in response to the current human power inside the second power interval when the current heart rate is lower than the target heart rate interval, and the first motor assistance is smaller than the second motor assistance.

17. The assistance controlling system of claim 16, wherein the operation processor further defines a third power interval corresponding to the plurality of preset health levels, and drives the assistance motor to output the third motor assistance in response to the current human power inside the third power interval, the second power interval is smaller than the third power interval.

18. The assistance controlling system of claim 11, wherein the operation processor further drives the assistance motor to output the third motor assistance in response to the current human power inside the first power interval, or drives the assistance motor to output a fourth motor assistance in response to the current human power inside the second power interval when the current heart rate is higher than the target heart rate interval, and the fourth motor assistance is greater than the third motor assistance.

19. The assistance controlling system of claim 18, wherein the operation processor further defines a third power interval corresponding to the plurality of preset health levels, and drives the assistance motor to output a fifth motor assistance in response to the current human power inside the third power interval, the second power interval is smaller than the third power interval, and the fifth motor assistance is greater than the fourth motor assistance.

20. The assistance controlling system of claim 11, wherein the motor assistance with different levels represents different operation efficiency of the assistance motor.

21. The assistance controlling system of claim 11, wherein the operation processor further defines a third power interval corresponding to the plurality of preset health levels, and drives the assistance motor to output a fourth motor assistance in response to the current human power inside the third power interval, the second power interval is smaller than the third power interval, and the fourth motor assistance is greater than the third motor assistance.

* * * * *